United States Patent [19]

Ortiz et al.

[11] Patent Number: 5,415,160

[45] Date of Patent: May 16, 1995

[54] SURGICAL LIFT METHOD AND APPARATUS

[75] Inventors: Mark S. Ortiz, Milford; Stephen J. Failla, Cincinnati, both of Ohio; Jean-Pierre Kinet, Ulzburg, Germany; Frederic Marie, Guise, France

[73] Assignee: Ethicon, Inc., Cincinnati, Ohio

[21] Appl. No.: 213,145

[22] Filed: Mar. 15, 1994

[51] Int. Cl.$^6$ ............................................. A61B 17/02
[52] U.S. Cl. ..................... 128/20; 606/149; 606/115; 5/624
[58] Field of Search ............... 606/219, 215, 216, 119, 606/149; 294/64.1, 64.3, 65, 1.1; 604/115, 186, 180; 128/20, 30.2

[56] References Cited

U.S. PATENT DOCUMENTS

| | | | |
|---|---|---|---|
| 22,551 | 1/1859 | Duchamn | 294/64.1 |
| 517,481 | 4/1894 | Pressey | 128/30.2 |
| 2,067,268 | 1/1937 | Hans | 128/30.2 |
| 2,204,738 | 6/1940 | Swan | 128/30.2 |
| 2,610,882 | 9/1952 | Sutliffe | 294/1.1 |
| 2,704,071 | 3/1955 | Becker | 604/115 |
| 2,841,148 | 7/1958 | Kadavy . | |
| 3,831,587 | 8/1974 | Boyd . | |
| 3,863,639 | 2/1975 | Kleaveland . | |
| 4,052,980 | 11/1977 | Grams et al. . | |
| 4,141,363 | 2/1979 | James et al. | 606/216 |
| 4,151,838 | 5/1979 | Crew . | |
| 4,232,660 | 11/1980 | Coles . | |
| 4,291,687 | 9/1981 | Sinnreich . | |
| 4,537,197 | 8/1985 | Hulka | 606/119 X |
| 4,610,243 | 9/1986 | Ray . | |
| 4,616,633 | 10/1986 | Vargas Garcia . | |
| 4,616,634 | 10/1986 | Vargas Garcia . | |
| 4,705,040 | 11/1987 | Mueller et al. . | |
| 4,815,468 | 3/1989 | Annand et al. | 606/216 |
| 4,917,427 | 4/1990 | Scaglia | 294/64.1 |
| 4,945,897 | 8/1990 | Greenstein et al. . | |
| 5,109,831 | 5/1992 | Forrest et al. | 128/20 |
| 5,149,162 | 9/1992 | Focke et al. | 294/64.1 |
| 5,151,086 | 2/1992 | Duh et al. . | |
| 5,183,033 | 2/1993 | Wilk | 128/20 |
| 5,188,609 | 2/1993 | Bayless et al. | 604/180 |

FOREIGN PATENT DOCUMENTS 0246086 5/1987 European Pat. Off. .
WO92/21291 12/1992 WIPO .
WO92/21292 12/1992 WIPO .

OTHER PUBLICATIONS

Kitano et al., "A Safe and Simple Method to Maintain a Clear Field of Vision During Laparoscopic Cholecystectomy" from *Surgical Endoscopy*, (1992), 6:197–198.

Hashimoto et al., "Laparoscopic Cholecystectomy: An Approach Without Pneumoperitoneum" from *Surgical Endoscopy*, (1993), 7:54–56.

Akimaru et al., "Subcutaneous Wire Traction Technique With $CO_2$ Insufflation For Laparoscopic Cholecystectomy" from *Journal of Laparoendoscopic Surgery*, (1993), 3:59–62.

Banting et al., "Abdominal Wall Lift" from *Surgical Endoscopy*, (1993), 7:57–59.

*Primary Examiner*—Peter A. Aschenbrenner
*Attorney, Agent, or Firm*—Dressler, Goldsmith, Shore & Milnamow, Ltd.

[57] ABSTRACT

A method and apparatus for lifting an abdominal wall during laparoscopic diagnostic and surgical procedures. The surgical lift device includes a gripping portion for contacting and holding an external skin surface adjacent the abdominal wall. The gripping portion is selectively detachable from the skin surface. The device further includes a lifting portion that extends outwardly from the gripping portion. In accordance with alternative embodiments, the gripping portion may comprise an adhesive sheet or a suction member and the lifting portion may comprise a wire member or a portion of a hook and loop-type fastener.

4 Claims, 4 Drawing Sheets

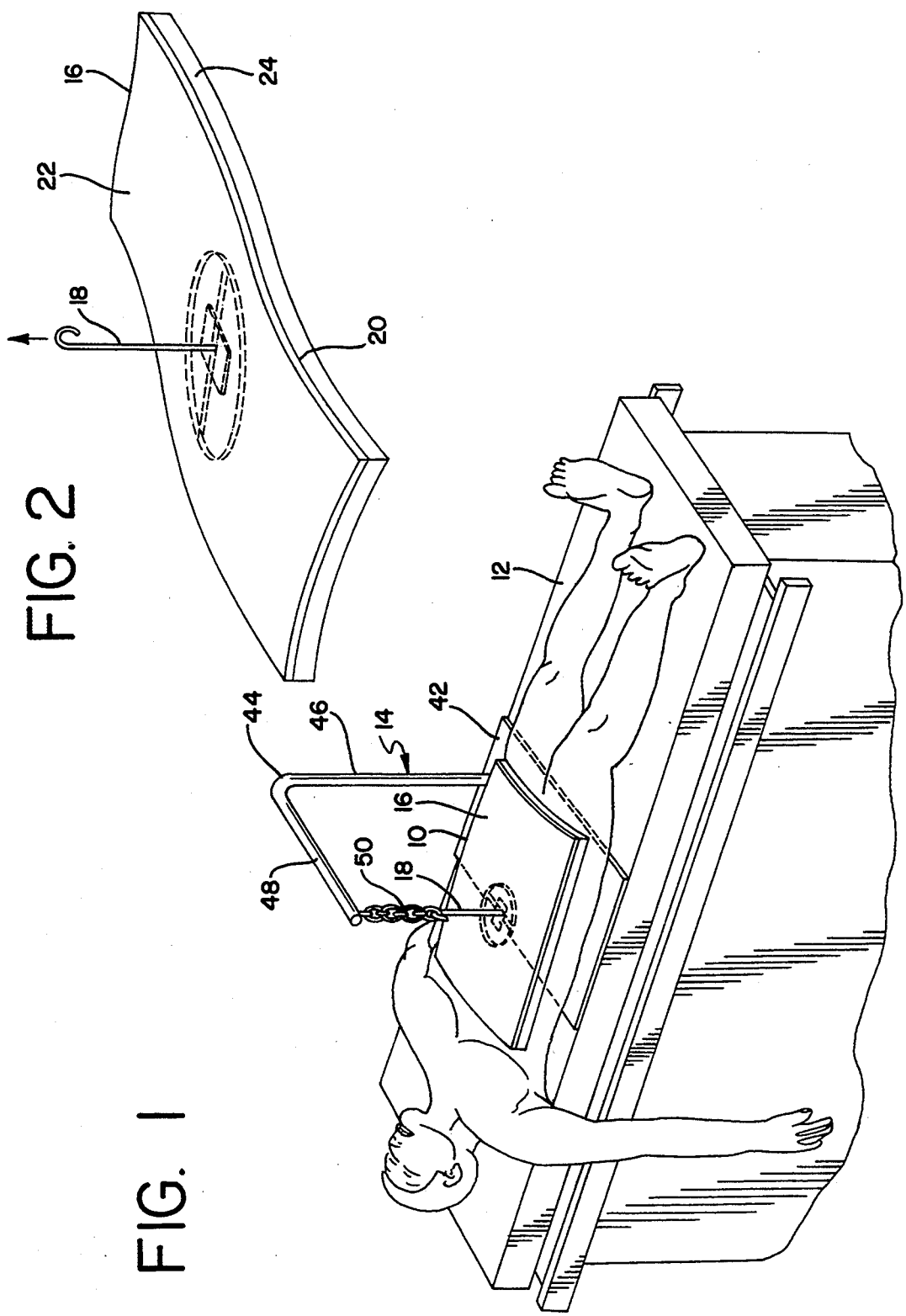

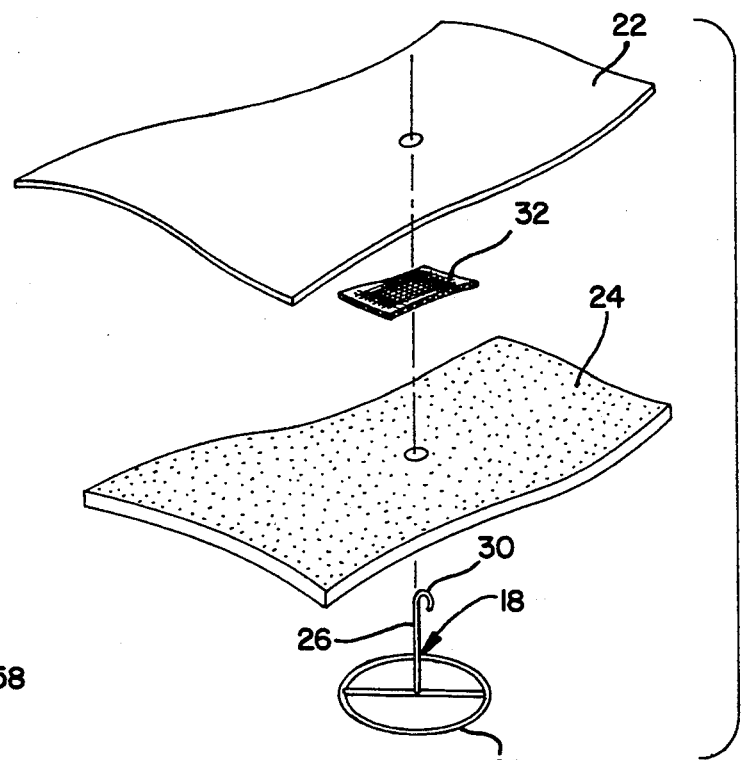
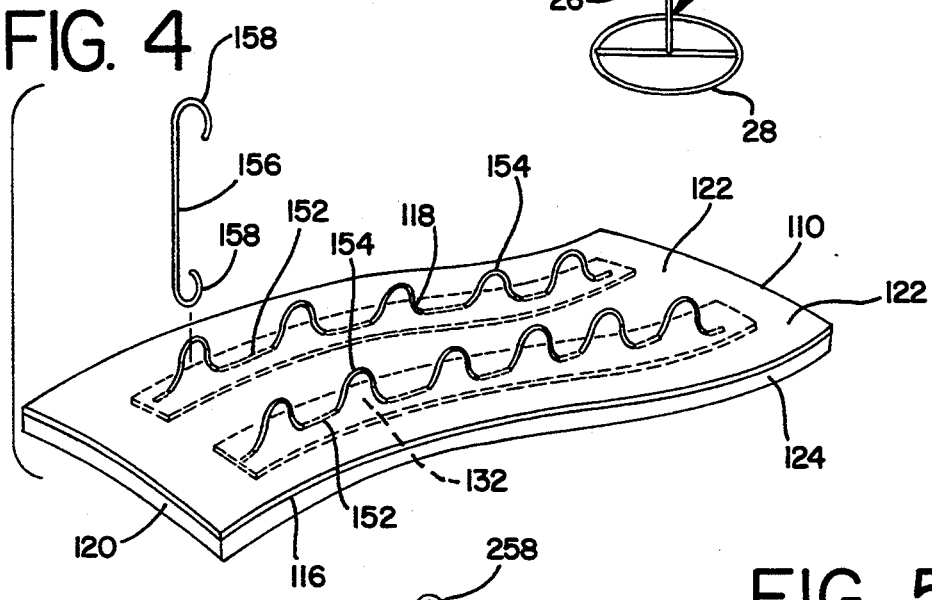
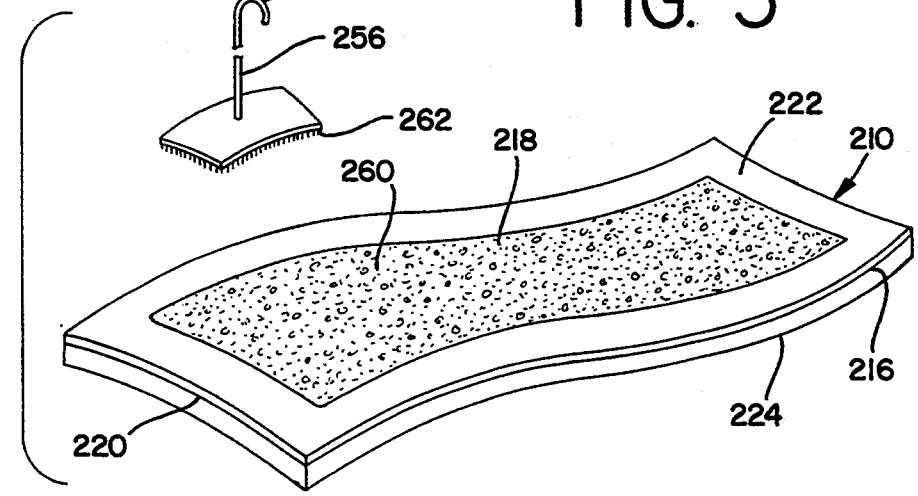

SURGICAL LIFT METHOD AND APPARATUS

FIELD OF THE INVENTION

This invention relates generally to surgical methods and devices and, more particularly, to methods and devices for lifting an abdominal wall during laparoscopic diagnostic and surgical procedures.

BACKGROUND OF THE INVENTION

Laparoscopic surgical procedures have been around for many years and have become more available due to advances in technology relating to the laparoscope or video imaging system. They are much less intrusive to the patient than typical open surgical procedures. While an open surgical procedure may involve one primary incision that is at least 5–25 centimeters long, a laparoscopic procedure typically uses smaller incisions, each only around 5–11 millimeters in length. In open surgery, the surgeon usually cuts muscle or fascia. In laparoscopic surgery, the surgeon generally does not cut muscle. Because they are less intrusive than open surgical procedures, laparoscopic procedures have resulted in much shorter surgical procedures and recovery times.

Laparoscopic procedures have typically involved insufflation of the abdominal or peritoneal cavity with carbon dioxide and/or other gases in order to create a pneumoperitoneum. The pneumoperitoneum establishes an open space inside the peritoneal cavity to enable the surgeon to move the laparoscope around and see inside.

Typically, the pneumoperitoneum is established by puncturing the abdominal wall with a Veress needle and injecting gas from an insufflator through the Veress needle into the peritoneal cavity to a pressure of around 12 mm Hg.

After insufflation, a trocar is advanced through the opening in the abdominal wall and into the peritoneal cavity. The trocar includes a tube or cannula that usually has a gaseous seal to contain the carbon dioxide within the peritoneal cavity and maintain insufflation. The cannula is used for insertion of other medical instruments such as a laparoscope therethrough and into the peritoneal cavity.

There may be certain difficulties associated with insufflation of the peritoneal cavity. First and foremost is postoperative pain which patients may experience in the abdomen or shoulder area due to migrating gas. This occurs when insufflation causes excess gas pressure in the peritoneal cavity. Excess gas pressure may also compress the pleural cavities thus making respiration difficult. Other possible difficulties associated with insufflation in laparoscopic surgery include subcutaneous emphysema, blood vessel penetration, etc.

The attendant difficulties of insufflation have led to alternatives to insufflation wherein a pneumoperitoneum is established by elevating the abdominal wall with a mechanical lift. The lift is introduced percutaneously into the peritoneal cavity before establishing a pneumoperitoneum. The lift is elevated mechanically in order to distend the abdomen. When the abdomen is distended, ambient air enters the peritoneum through the puncture opening in the abdomen and a pneumoperitoneum at or near ambient air pressure is established.

By establishing a pneumoperitoneum at ambient air pressure, insufflation and the concomitant need for gaseous seals in endoscopic instruments and trocars for maintaining a relatively high gas pressure in the peritoneal cavity is eliminated. Thus the attendant pain and difficulties of insufflation, as well as the need for costly equipment, is eliminated.

The prior art includes several abdominal lift structures. Origin Medsystems, Inc. of Menlo Park, Calif. markets a lift under the trademark Laparofan ™. It has two radially extending blades that are rotatable. The blades are closed together for initial insertion into the abdominal cavity. After insertion, the blades are spread or fanned. When the lift is elevated, the blades contact and elevate the inner surface of the abdominal wall. Origin's device is described in International Patent application PCT/FR91/4456.

Societe 3X, a French company, markets an abdominal lift and support structure. The lift is shown and described in International Patent Application PCT/FR91/227. It is a bar comprising a series of bends, forming a generally triangular shape. The distal tip of the lift is turned downwardly slightly. The support structure has a crane and boom design. Gross adjustments are made by sliding the supporting leg and the boom within their respective holders. A mechanical screw-jack is used for fine adjustment.

International Patent Application PCT/FR91/227 describes an abdominal lift having various curves in different directions. U.S. Patent No. 5,183,033 describes a method for lifting an abdominal wall with a set of linear and non-linear abdominal lifts. International Patent Application PCT/US/4392 describes a variety of mechanical rods, arms and/or balloons for mechanically lifting an abdominal wall during laparoscopic surgery.

There are some other prior art structures for elevating and/or supporting abdominal lifts in laparoscopic surgery. U.S. Pat. No. 5,183,033 illustrates support structures using winches or U-shaped bars for use in laparoscopic surgery.

Further, there are a number of prior art support structures for supporting mechanical lifts used in open surgery. For example, see U.S. Pat. Nos. 5,109,831 and 4,143,652.

An improved abdominal lift device is disclosed in U.S. patent Ser. No. 08/108,895, filed on Aug. 18, 1993, and assigned to the same assignee as the present invention. The device includes a curved portion that defines a substantial portion of a circle. A spoke portion extends radially inwardly from the curved portion and an upstanding member extends upwardly from the spoke portion. The upstanding member is connectable to a support structure which elevates and supports the abdominal lift device.

The ease of operation oft most of these prior art lift devices without any damage to internal viscera is limited. There is also a need for an alternative surgical lift method and device that may be used by doctors in their offices for diagnostic purposes. It is anticipated that such diagnostic procedures may include the use of a Veress needle-type device having optical capabilities without the use of a general anesthesia.

SUMMARY OF THE INVENTION

The present invention provides a surgical lift device that includes a gripping portion for contacting and holding an external skin surface adjacent the abdominal wall. The gripping portion provides a gripping force that is sufficient to permit lifting of the abdominal wall to an elevated position and to hold the abdominal wall in such elevated position. The gripping portion is selectively detachable from the skin surface. The device further includes a lifting portion that extends upwardly from the gripping portion.

In accordance with a preferred embodiment, the gripping portion comprises an adhesive sheet having a backing portion with an adhesive coating applied thereto. The adhesive coating may be a hydrogel or other suitable adhesive material. The lifting portion may include one or more vertically extending wire members extending from the gripping portion.

In accordance with an alternative embodiment of the invention, the lifting portion may include a loop portion of a hook and loop-type fastener attached to the gripping portion for connection to a cooperating loop portion associated with a support arrangement.

In accordance with a further alternative embodiment of the invention, the gripping portion may include a suction member that defines a vacuum chamber. The suction member is in periodic or continuous communication with a vacuum source.

The invention further comprises a unique method for lifting and holding an abdominal wall portion of a human body in an elevated position to perform a diagnostic or surgical procedure in an abdominal cavity. A surgical lift device is attached to an external skin surface adjacent the internal abdominal wall. The surgical lift device is lifted and held in an elevated position so as to hold the abdominal wall in an elevated position. After the diagnostic or surgical procedure is performed with an optical device and obtain other instruments directed into the abdominal cavity, the surgical lift device is detached from the external skin surface.

These and other aspects and attributes of the present invention will be discussed with reference to the following drawings and accompanying specification.

BRIEF DESCRIPTION OF THE DRAWINGS

FIG. 1 is a perspective view of a patient lying on an operating table, having a surgical lift device constructed in accordance with the invention applied thereto, that is supported by a support structure;

FIG. 2 is a perspective view of the surgical lift device as shown in FIG. 1;

FIG. 3 is an exploded perspective view of the surgical lift device as shown in FIG. 2;

FIG. 4 is a perspective view of an alternative embodiment of a surgical lift device in accordance with the invention;

FIG. 5 is a perspective view of another alternative embodiment of a surgical lift device in accordance with the invention;

DETAILED DESCRIPTION OF THE INVENTION

Figure 6:
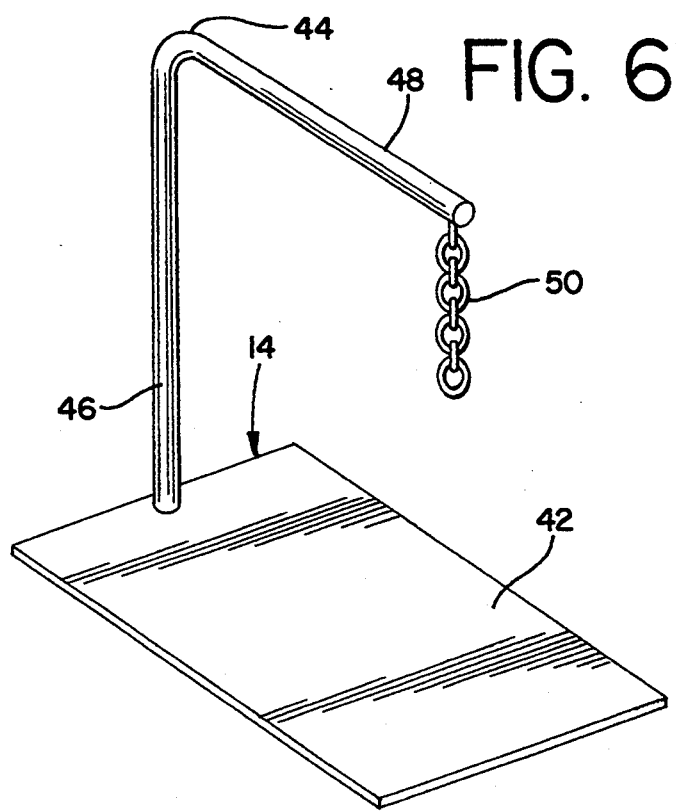
FIG. 6 is a perspective view of a support structure constructed in accordance with the invention for supporting a surgical lift device in an elevated position.

While this invention is susceptible of embodiment in many forms, there is shown in the drawings, and will be described herein in detail, specific embodiments thereof with the understanding that the present disclosure is to be considered as an exemplification of the principles of the invention and is not intended to limit the invention to the specifically illustrated embodiments.

Referring to FIGS. 1–3, a surgical or abdominal lift device 10 is shown in accordance with the invention in cooperation with a doctor's office or operating room table 12 and a support structure 14.

Lift device 10 comprises a gripping portion 16 and a lifting portion 18. Gripping portion 16 includes an adhesive sheet 20 having a backing portion 22 and an adhesive coating 24 applied to the backing portion. Sheet 20 may be of different shapes and sizes depending upon the particular medical procedure to be performed and the size of the patient. As shown, sheet 20 is of a rectangular shape and of a size that preferably substantially covers the abdominal area of the patient.

In accordance with a preferred embodiment of the invention, the backing portion 22 is made from PEBAX ® polymethylmethacrylate. Alternatively, backing portion 22 may be made from another medical grade tear resistant flexible polymer. The adhesive coating 24 is preferably a hydrogel material such as PROMEON ® RG63X. It is necessary that the backing portion 22 and the coating 24 provide a gripping force sufficient to permit lifting of an abdominal wall to an elevated position and to hold the abdominal wall in the elevated position. It is also necessary that the adhesive coating have adhesive properties that permit the detachment of the sheet 20 from the external skin surface adjacent the abdominal wall without undue injury to the skin.

In accordance with a preferred embodiment the lifting portion 18 comprises a wire member 26 that extends vertically upward from a generally circular base member 28. Wire member 26 extends through a central portion of sheet 20 and is provided with a hook portion 30 at its distal end. A reinforcing layer or sheet 32 may be provided adjacent the gripping portion 16 for reinforcing the connection between the gripping portion and the wire member 26. Although only one wire member 26 is shown, a plurality of spaced apart wire members may be provided.

Referring to FIG. 6, there is shown a preferred embodiment of a support structure 14 that is designed to cooperate with lift device 10. Support structure 14 includes a generally rectangular plate or base member 42 that is dimensioned to extend substantially across table 12. An L-shaped support member 44, having a substantially vertical portion 46 and a transverse portion 48, extends from base member 42 such that transverse portion 48 extends above the surface of base member 42. The distal end of transverse portion 48 is positioned above a central portion of base member 42 and is provided with a linked chain 50 that extends downwardly therefrom.

Referring to FIG. 1, in use the support structure 14 is positioned on the table 12 such that the base member 42 extends across a center portion of the table. The patient is positioned on the table on top of base member 42 such that transverse portion 48 extends across the table in a manner so that chain 50 is located in vertical alignment with a .center portion of the patient's abdomen. The lift device 10 is applied to the external surface of the patient's skin adjacent the abdominal wall. The adhesive coating 24 attaches the sheet 20 to the external skin surface upon the application of downward pressure thereto. The wire member 26 of lifting portion 18 extends upwardly towards the chain 50.

The doctor may then grasp the lifting portion 18 and apply an upward force thereto to lift the device 10 and thereby elevate the abdominal wall to a desired elevated position. The hook portion 30 is attached to an appropriate link of chain 50 to hold the lift device and abdominal wall in a desired elevated position. The doctor may then perform the necessary diagnostic or surgical procedure using various devices that are directed into the abdominal cavity. For example, an optical Veress needle may be directed into the abdominal cavity to perform a diagnostic procedure within a doctor's office without the use of a general anesthesia. Similarly, one of many well known laparoscopic surgical procedures may be performed in an operating room under a general anesthesia. The instruments may be directed through the access holes that are cut through or preformed through the lift device.

Upon completion of the diagnostic or surgical procedure, the wire member 26 is released from the chain 50 and the device 10 is lowered returning the abdominal wall to its normal position. The device 10 is then detached from the patient by peeling it off the external skin surface.

Referring to FIG. 4, there is shown an alternative embodiment of a lift device of the present invention indicated at 110. Embodiments 10 and 110 are similarly constructed and corresponding components thereof are indicated by reference numerals having the same last two digits. Except where otherwise indicated, the above disclosure with respect to such common components are incorporated herein by reference with respect to lift device 10.

Lift device 110 comprises a gripping portion 116 and a lifting portion 118. Gripping portion 116 includes an adhesive sheet 120 having a backing portion 122 and an adhesive coating 124 applied to the backing portion.

A pair of spaced apart generally parallel wire members 152 are positioned between the backing portion 122 and the adhesive coating 124 such that a plurality of loop portions 154 thereof extend outwardly from the outer surface of backing portion 122. A reinforcing layer or sheet 132 may be provided between backing portion 122 and adhesive coating 124. A plurality of hook members 156 may be provided, only one of which is shown. Members 156 have hook portions 158 at both ends thereof for receiving a loop portion 154 at one end and a cooperating portion of a support structure at the other end.

During use of lift device 110 in a similar manner as discussed above with respect to device 10, depending on the particular procedure being performed, the lift device 110 may be lifted by one or more members 156 positioned in selected loop portions 154 to effect the desired lifting of the abdominal wall.

Referring to FIG. 5 there is shown another alternative embodiment of a lift device of the present invention indicated at 210. Embodiments, 10, 110 and 210 are similarly constructed and corresponding components thereof are indicated by reference numerals having the same last two digits. Except where otherwise indicated, the above disclosure with respect to such common components are incorporated herein by reference with respect to lift device 210.

Lift device 210 comprises a gripping portion 216 and a lifting portion 218. Gripping portion 216 includes an adhesive sheet 220 having a backing portion 222 and an adhesive coating 224 applied to the backing portion.

The exterior surface of backing portion 222 is provided with a lifting portion 218 comprising a loop portion 260 of a hook and loop-type fastener, such as a Velcro TM fastener. A plurality of hook members 256 may be provided, only one of which is shown. Members 256 have a hook portion 258 at one end thereof and a hook portion 262 of the hook and loop-type fastener at the other end thereof. The use of lift device 210 is similar to that discussed above with respect to lift device 110 except that the hook portion 262 is attached to a selected portion of loop portion 260 to effect the desired lifting of the abdominal wall.

Figure 7:
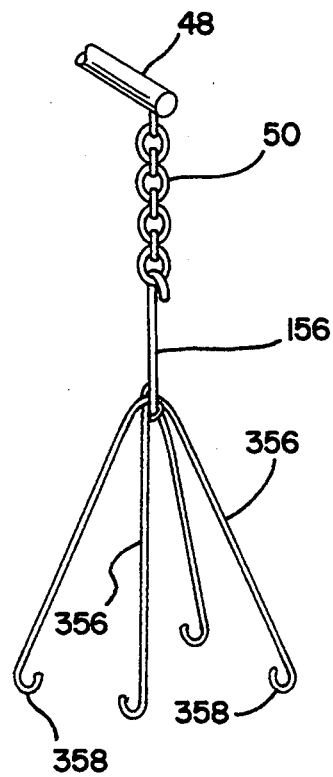
FIG. 7 is a perspective view of a portion of the support structure as shown in FIG. 6 showing a plurality of hook members for attachment to a plurality of sections of a surgical lift device.

In order to accommodate the lifting of lift device 110, wherein the device is lifted from a multiple portions thereof, the support structure 14 may be provided with one or more bent wire members 356 that have hook portions 358 at the respective ends thereof, as shown in FIG. 7. The hook portions 358 may be attached to a corresponding loop portion 154 of lift device 110. The support structure as shown in FIG. 7 may be alternatively provided with hook portions of a hook and loop-type fastener at the ends of the wire members 356 (not shown) for attachment to a lift device 310.

Figure 8:
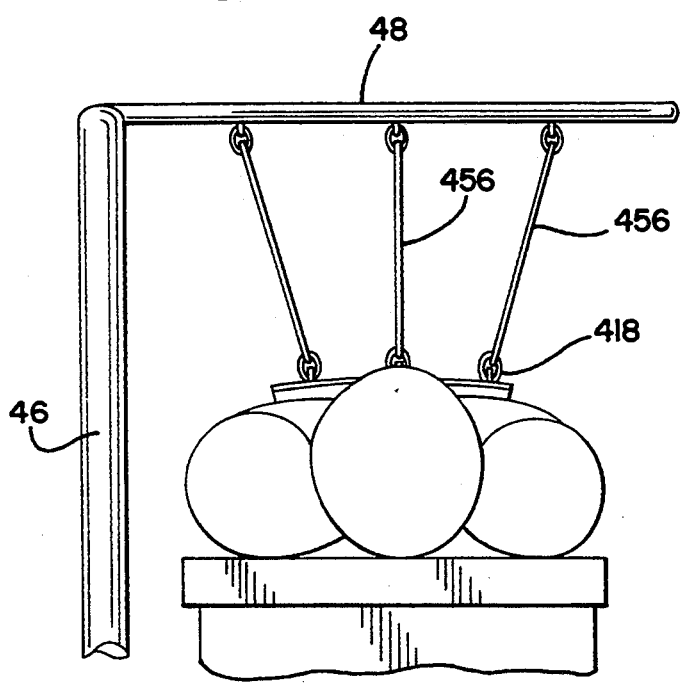
FIG. 8 is an elevational view of a portion of an alternative embodiment of a support structure in accordance with the invention.

Referring to FIG. 8, a support structure 114 is shown for supporting a lift device of the type disclosed above, wherein a plurality of downwardly extending, transversely spaced apart, wire members 456 extend downwardly from transverse portion 48 for attachment to a lift device of the type discussed above having cooperating lifting portions 418.

Figure 9:
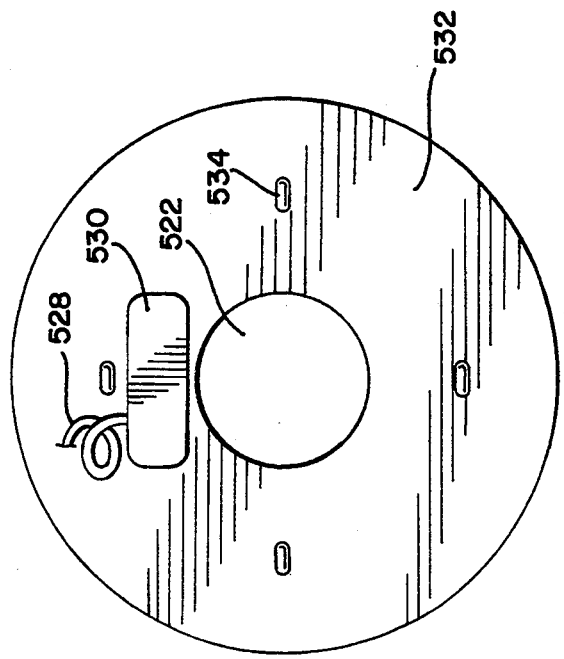
FIG. 9 is a perspective view of a further embodiment of a surgical lift device in accordance with the invention.
Figure 10:
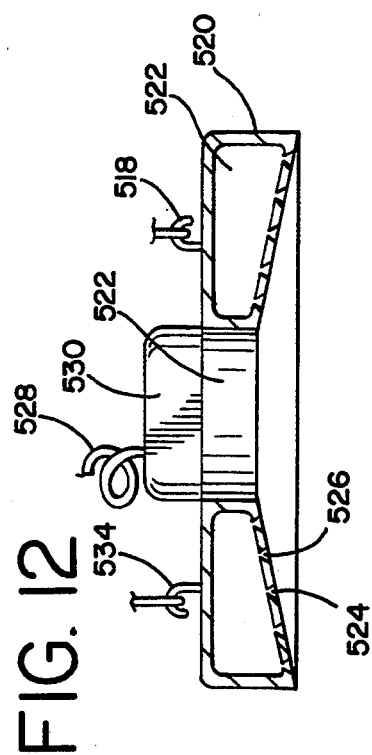
FIG. 10 is a top plan view of the device shown in FIG. 9.
Figure 11:
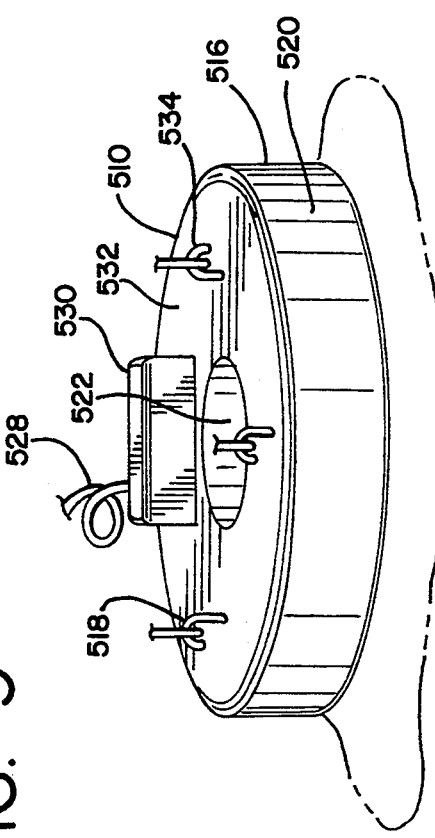
FIG. 11 is a cross-sectional view taken along line 11—11 in FIG. 9.

Referring to FIGS. 9–11, there is shown a further alternative embodiment of a lift device of the present invention indicated at 510. Lift device 510 utilizes suction for gripping the external skin surface adjacent the abdominal wall.

Lift device 510 comprises a gripping portion 516 and a lifting portion 518. Gripping portion 516 includes a generally annular vacuum manifold 520 that defines a central open area 522 that extends therethrough. Manifold 520 has a lower surface 524 that is provided with a plurality of small, spaced apart openings 525 that communicate with the interior of manifold 520.

Figure 12:
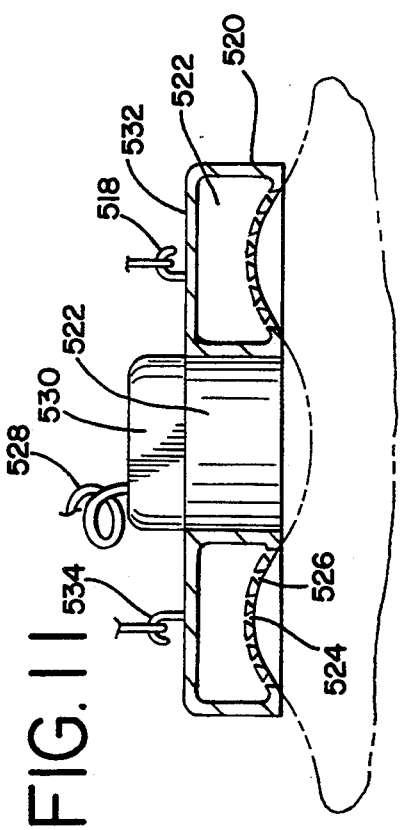
FIG. 12 is a cross-sectional view similar to FIG. 11 showing an alternative embodiment of a surgical lift device.

Manifold 520 communicates with a suitable vacuum source (not shown) through control valve 530 and a vacuum line 528. Control valve 530 is a conventional valve of the type that may be preset to control the vacuum level in the manifold to a level that will minimize capillary bursting at the skin surface. Inner surface 524 may be formed as a segment of a torso, as shown in FIG. 11, or as an inwardly inclined surface such as a segment of a cone, as shown in FIG. 12, to other suitable shapes to conform to the abdomen. Although not specifically shown, it is contemplated that manifold 520 may comprise one or more spaced apart rectangular or curvilinear manifold segments.

The upper surface 532 of the lift device 510 is provided with a lifting portion 518. Lifting portion 518 may comprise a plurality of spaced apart lifting hook members 534 that extend upwardly from surface 532. In a similar manner as discussed above with respect to the other embodiments of the invention, it is intended that lift device 510 be supported by a suitable support structure of the type generally discussed above. During use of lift device 510 in a similar manner as discussed above, it is anticipated that diagnostic or surgical instruments or devices may be extended through open area 522.

From the foregoing, it will be observed that numerous modifications and corrections can be effected without departing from the true spirit and scope of the novel concepts of the present invention. It will be understood that no limitation with respect to the specific embodiments illustrated herein is intended or should be inferred. It is, of course, intended to cover by the appended claims all such modifications as fall within the scope of the claims.

What is claimed is:

1. A method for lifting and holding an abdominal wall portion of a human body in an elevated position to perform a diagnostic or surgical procedure in an abdominal cavity, said method comprising the steps of:
   (a) attaching a surgical lift device to an external skin surface adjacent the abdominal wall of a human body;
   (b) lifting and holding the surgical lift device in an elevated position so as to hold the abdominal wall in an elevated position to establish an open space inside the peritoneal cavity;
   (c) performing a diagnostic or surgical procedure in the abdominal cavity; and
   (d) detaching the surgical lift device from the external skin surface.

2. The method as defined in claim 1 further including the step of directing an optical device into the abdominal cavity.

3. A surgical lift device, comprising:
   a gripping portion for contacting and holding an external skin surface adjacent the abdominal wall of a human body, said gripping portion having a gripping force sufficient to permit lifting of said abdominal wall to an elevated position and to hold said abdominal wall in said elevated position, said gripping portion being detachable from said skin surface; and
   a lifting portion extending upwardly frown said gripping portion, said lifting portion includes a first portion of a hook and loop-type fastener attached to said gripping portion for connection to a cooperating second position of a hook and loop-type fastener associated with a support structure.

4. A surgical lift device, comprising:
   a gripping portion for contacting and holding an external skin surface adjacent the abdominal wall of a human body, said gripping portion having a gripping force sufficient to permit lifting of said abdominal wall to an elevated position and to hold said abdominal wall in said elevated position, said gripping portion being detachable from said skin surface; and
   a lifting portion extending upwardly from said gripping portion, said lifting portion includes a plurality of outwardly extending connecting loop segments for connection to a cooperating hook member associated with a lift structure.

* * * * *